United States Patent
Light et al.

(10) Patent No.: US 8,358,126 B2
(45) Date of Patent: Jan. 22, 2013

(54) MAGNETOSTRICTIVE SENSOR FOR TANK FLOOR INSPECTION

(75) Inventors: Glenn M Light, San Antonio, TX (US); Alan R Puchot, San Antonio, TX (US); Adam C Cobb, San Antonio, TX (US); Erika C Laiche, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 642 days.

(21) Appl. No.: 12/687,727

(22) Filed: Jan. 14, 2010

(65) Prior Publication Data

US 2011/0169486 A1 Jul. 14, 2011

(51) Int. Cl.
*G01N 27/82* (2006.01)

(52) U.S. Cl. ........ 324/240; 324/228; 324/229; 324/230; 324/237; 324/238; 324/219; 324/222; 324/220; 73/622; 73/624; 73/625; 73/623; 73/627; 73/628; 73/629

(58) Field of Classification Search .................. 324/240, 324/228, 229, 230, 237, 238, 219, 222, 220; 73/622, 624, 625, 623, 627, 628, 629
See application file for complete search history.

(56) References Cited

U.S. PATENT DOCUMENTS

| | | | | |
|---|---|---|---|---|
| 2,573,799 A | * | 11/1951 | MacLean | 324/219 |
| 4,797,614 A | * | 1/1989 | Nelson | 324/236 |
| 5,456,113 A | * | 10/1995 | Kwun et al. | 73/587 |
| 5,648,721 A | * | 7/1997 | Wincheski et al. | 324/240 |
| 5,884,709 A | * | 3/1999 | Evans et al. | 169/46 |
| 6,002,251 A | * | 12/1999 | Sun | 324/240 |
| 6,295,677 B1 | * | 10/2001 | Kwun et al. | 73/602 |
| 6,373,245 B1 | * | 4/2002 | Kwun et al. | 324/240 |
| 6,624,628 B1 | * | 9/2003 | Kwun et al. | 324/240 |
| 6,868,730 B2 | * | 3/2005 | Kim et al. | 73/643 |

(Continued)

OTHER PUBLICATIONS

Shaikh et al., "Failure of Above Ground Storage Tanks: A Study", 2007 International Corrosion Conference & Expo (Paper No. 07044), pp. 1-16.*

(Continued)

*Primary Examiner* — Jermele M Hollington
*Assistant Examiner* — Lamarr Brown
(74) *Attorney, Agent, or Firm* — Chowdhury & Georgakis PC; Ann C Livingston

(57) ABSTRACT

A method of testing for defects in the bottom of an above ground storage tank, the tank bottom having a lip extending outwardly from the tank wall around the circumference of the tank. A special magnetostrictive sensor is designed to be placed on this lip. The sensor is placed over a strip of magnetostrictive material, which generally conforms in length and width to the bottom of the probe, with a couplant being applied between the strip and the lip surface. The sensor is then operated in pulse echo mode to receive signals from defects in the bottom of the tank. It is incrementally moved around the circumference of the tank.

12 Claims, 4 Drawing Sheets

U.S. PATENT DOCUMENTS

| | | | |
|---|---|---|---|
| 6,917,196 B2* | 7/2005 | Kwun et al. | 324/240 |
| 6,925,881 B1* | 8/2005 | Kwun et al. | 73/600 |
| 7,019,518 B2* | 3/2006 | Amini et al. | 324/229 |
| 7,474,092 B1* | 1/2009 | Kwun et al. | 324/238 |
| 8,156,812 B2* | 4/2012 | Tomar et al. | 73/602 |
| 2002/0043973 A1* | 4/2002 | Amini et al. | 324/229 |
| 2002/0105324 A1* | 8/2002 | Kwun et al. | 324/240 |
| 2004/0095137 A1* | 5/2004 | Kwun et al. | 324/240 |
| 2005/0104584 A1* | 5/2005 | Kwun et al. | 324/238 |
| 2008/0315872 A1* | 12/2008 | Kwun et al. | 324/262 |
| 2009/0174399 A1* | 7/2009 | Vinogrador | 324/238 |
| 2009/0229362 A1* | 9/2009 | Tomar et al. | 73/592 |
| 2010/0052669 A1* | 3/2010 | Kwun et al. | 324/240 |
| 2010/0295565 A1* | 11/2010 | Drack | 324/693 |
| 2011/0308316 A1* | 12/2011 | Miki et al. | 73/622 |

OTHER PUBLICATIONS

Ali et al., "Above Ground Tank Bottom Corrosion Due to Inappropriate Construction Practices and Corrosion Control Using Cathodic Protection", Corrosion 1998 (Paper No. 596), pp. 1-11.*

Schempf_1994, "Above-Ground Storage Tank Inspection Robot System", IEEE International Conference Robotics and Automation 1994, pp. 1403-1408.*

Sun et al., "Review of On-line Defects Detection Technique for Above Ground Storage Tank Floor Monitoring", IEEE Proceedings of the 8th World Congress on Intelligent Control and Automation Jul. 6-9, 2010, pp. 4178-4181.*

* cited by examiner

MAGNETOSTRICTIVE SENSOR FOR TANK FLOOR INSPECTION

TECHNICAL FIELD OF THE INVENTION

This invention relates to nondestructive testing of the bottom surface of large above-ground storage tanks, and more particularly to use of a magnetostrictive sensor for such applications.

BACKGROUND OF THE INVENTION

Magnetostriction is a property of ferromagnetic materials that causes them to change shape when subjected to a magnetic field. Magnetostrictive materials can convert magnetic energy into kinetic energy, or the reverse, and are used to build various actuators and sensors.

Magnetostrictive sensors have been developed for nondestructive materials testing that make use of magnetostrictive properties of the material under inspection. These magnetostrictive sensors for testing ferromagnetic materials, and can also be made to work on nonferromagnetic metals by providing a ferromagnetic material at areas where the sensors are to be placed. This may be achieved, for example, by coating the surface of the material to be tested with a coat of ferromagnetic material or bonding a ferromagnetic medium such as wire or ribbon to the surface of the material.

The combination of a magnetized magnetostrictive material and an excitation coil produces a magnetostrictive sensor (MsS) probe. For active non-destructive testing, elastic waves are launched and reflected echoes of the waves from defects such as corrosion or cracks are detected. A good example of this is the inspection of pipes and tubes, the primary structural members used in various industries to transport gaseous or liquid products.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The invention described herein is directed to a new application of MsS (magnetostrictive sensor) technology. This new application is for "plate" inspection, specifically, inspection of above-ground tank bottom floors.

For plate applications, the conventional practice for MsS inspection and monitoring is the bonding of a magnetostrictive strip material to the surface of the part being inspected or monitored. However, it is not practical or cost effective to bond magnetostrictive material to a tank bottom floor. This new application uses a specially designed MsS sensor.

Figure 1:
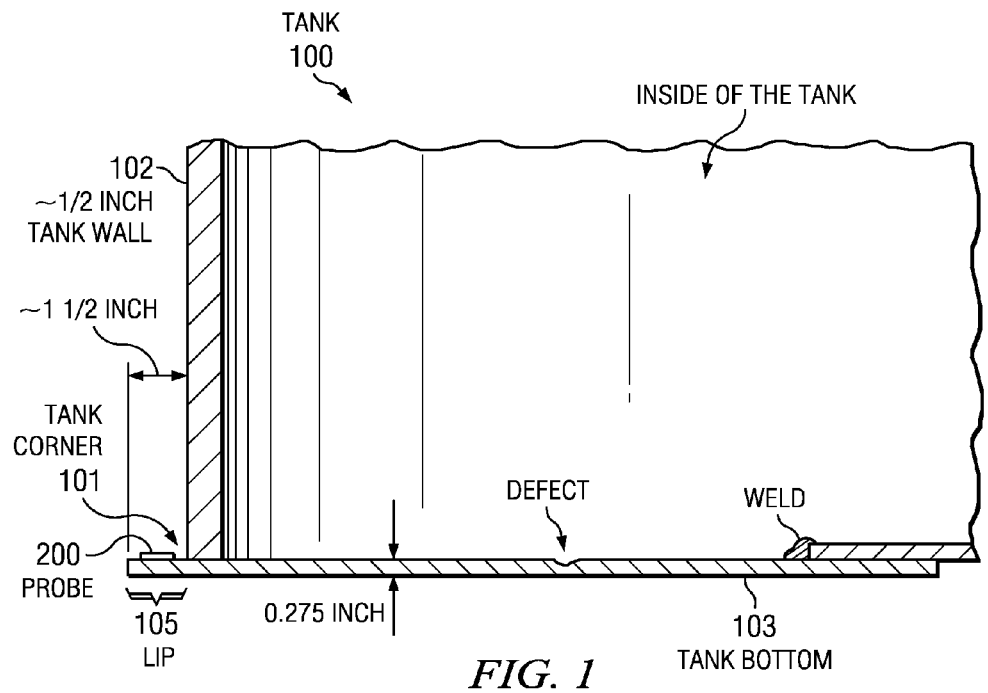
FIG. 1 illustrates a portion of an above ground storage tank with a sensor in place for testing in accordance with the invention.

FIG. 1 illustrates a cross section of portion of an above-ground tank suitable for use with an MsS sensor 200 of the type described herein. The portion illustrated is the bottom corner 101 of the tank, as well as a portion of the tank wall 102 and tank bottom 103. In this example, the tank wall thickness is 0.5 inch, and the tank bottom thickness is 0.275 inches. A tank bottom 103 typically comprises multiple plates, which are joined together using fillet type welds.

Figure 2:
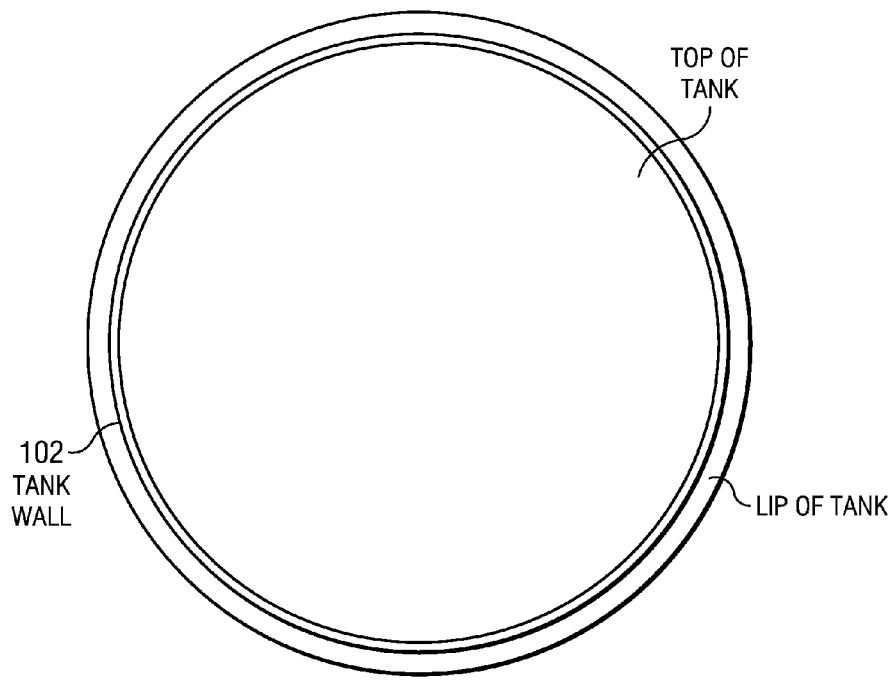
FIG. 2 is a top view of a storage tank, suitable for testing in accordance with the invention.

FIG. 2 is a top plan view of tank 100, showing wall 102 and lip 105 at the bottom of the tank. Referring to both FIGS. 1 and 2, it is assumed that tank 100 has a lip 105, which is typically an extension of the outer plate of tank bottom 103 outwardly past the tank wall 102.

It is upon this lip 105 that sensor 200 is placed. A typical width of lip 105 (measured outwardly from the outer surface of wall 102) is 1½ inches. As explained below, this width accommodates at least the narrow dimension of sensor 200.

It can be easily understood, that for testing for defects in the bottom of tank 100 it would not make sense to bond magnetostrictive material to the lip 105. Tanks such as tank 100 can be 100 feet in diameter, which would mean that approximately 314 linear feet of material would have to been bonded to the tank and left in place.

Instead, as explained below in further detail, sensor 200 is placed on lip 105 and is scanned around the edge of the tank to inspect the bottom plates inwardly beyond the tank wall 102. A shear wave couplant applied between the sensor 200 and the surface of the lip 105 facilitates this capability.

Figure 3:
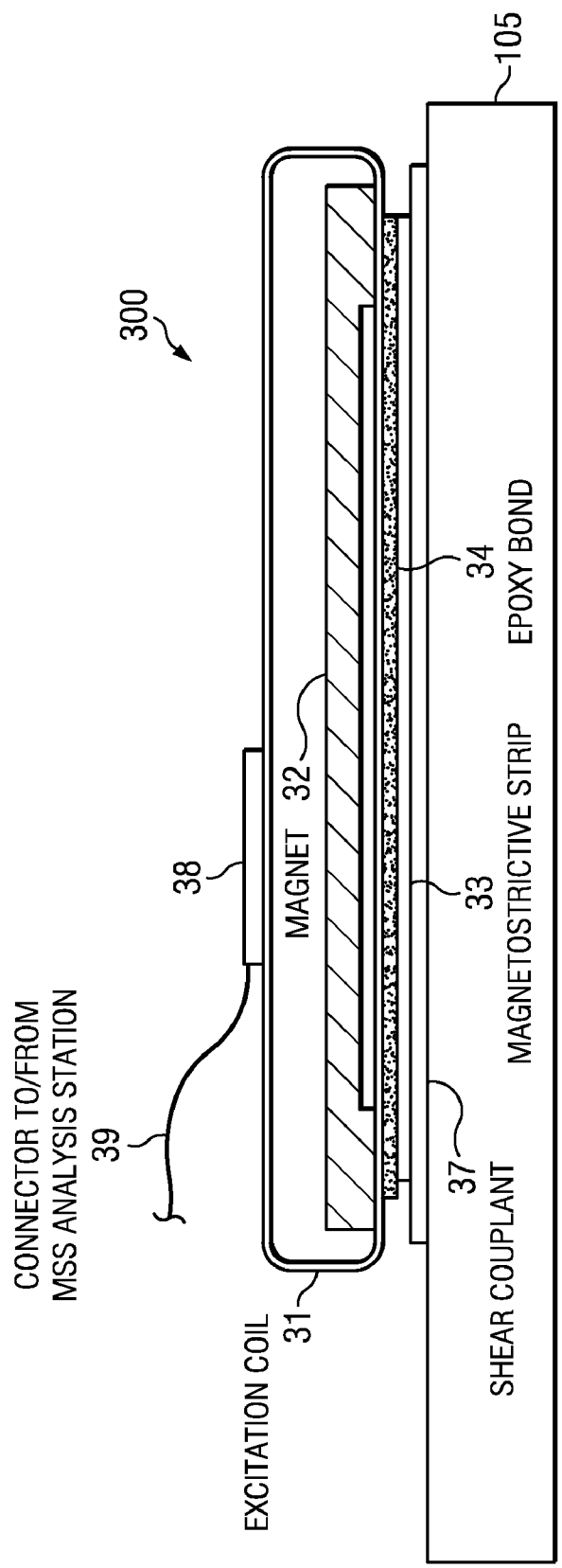
FIG. 3 illustrates the operating components of one embodiment of a magnetostrictive sensor in accordance with the invention.

FIG. 3 illustrates the electrical components of one embodiment of sensor 200, identified as sensor 300. Sensor 300 is illustrated with its associated magnetostrictive strip 33. It is further illustrated as used for testing, placed on a lip 105 of a tank 100.

Sensor 300 operates in accordance with basic MsS technology, applied for the generation and reception of guided waves. When a ferromagnetic material is placed in a biasing magnetic field and then subjected to a time varying magnetic field, the magnetic domains in the material produce a mechanical wave (known as the Joule Effect). If the magnetic field is varied at a frequency greater than 20 kHz, the generated wave will be an ultrasonic wave. For wave detection, mechanical stress (or strain) causes a change in magnetic induction of the ferromagnetic material and the coil is used to receive the signal (known as the Villari effect).

The orientation of the biasing magnetic field with respect to the time varying magnetic field affects the mode of wave generated. Longitudinal modes are generated when the biasing magnetic field is normal to the windings of the excitation coil. Shear modes are generated when the biasing magnetic field is parallel to the windings of the excitation coil.

Most work conducted in pipes and plates that have liquid contacting one surface is done with shear modes to prevent the transfer of energy into liquid so that the wave stays in the metal. As the shear wave propagates in the pipe wall or plate, it interacts with variation in that wall caused by corrosion or cracking (defect). Because the shear wave travels at a velocity governed by the dispersion curve and because the wave is reflected back to the sensor by the variation in the wall, the timing of the reflection can be used to locate the defect relative to the sensor. Also, because the frequencies used for this type of inspection are usually low, the wave can travel many feet and provide a long range inspection capability relative to the sensor.

Sensor 300 comprises an excitation coil 31 wrapped around the long dimension of a rectangular u-shaped magnet 32. In other embodiments, the wrapping of the coil relative to the magnet could be in different configurations, with the common characteristic being the orientation of the AC (coil-induced) and DC (bias magnet) fields for the generation of shear mode waves, as discussed above.

Where magnet 32 is horseshoe-shaped, having a length from end to end, coil 31 is wrapped around this long dimension of magnet 32. Other configurations may be possible, with the orientation of magnet 32 relative to the excitation coil 31, and how it is achieved in the sensor being important features of sensor 300 for the reasons discussed above.

Coil 31 may comprise a ribbon cable, a number of windings about bobbin, or other means of providing an electromagnetic coil. The size and electrical parameters of coil 31 may be experimentally determined by the specific characteristics of the tanks to be tested.

A magnetostrictive strip 33 is bonded to the bottom of sensor 300. An example of a suitable bonding material is an epoxy, as illustrated by layer 34 between sensor 300 and strip 33.

An example of a suitable magnetostrictive material is FeCo. Strip 33 has width and length dimensions substantially the same as, or slightly smaller than, that of the bottom surface of sensor 300.

An example bottom dimension of sensor 300 is 5.25 inch(es)×1.1 inches. For this size probe, a typical thickness of strip 33 is 0.006 inch. Also, for a sensor this size, the magnetostrictive material would typically have dimensions of 5 inch×1 inch.

Coil 31 inductively applies a time varying magnetic field and detects a magnetization change in the material under test. Magnet 32 provides DC bias magnetic fields to the magnetostrictive strip 33. The DC bias magnetic fields are used to enhance the efficiency of the energy transduction between electric and mechanical energies and to make the frequency of the elastic wave follow that of the electrical signals and vice versa.

Sensor 300 may have appropriate circuitry 38 for implementing MsS excitation and detection, and has a connection 39 to appropriate MsS instrumentation. For example, circuitry 38 may comprises signal conditioning circuitry for receiving and conditioning a coil excitation signal.

A couplant 37 is placed on the lip 105 beneath the desired location of sensor 300 and strip 33. Various shear wave couplant substances may be used. In general, the couplant is a non-newtonian fluid, such as honey or similar to honey, that supports shear, or transverse, wave motions. An example of a suitable product is the Panametrics-NDT SWC couplant.

In operation, MsS sensor 300 operates in a pulse-echo mode, so that one sensor 300 both transmits and receives. Elastic guided waves in ultrasonic frequencies are generated and propagated into the bottom plates of the tank, and waves reflected from structure defects are detected. Sensor 300 delivers the signal to MsS analysis equipment. The occurrence time of a defect signal (from the time of initial pulse) and the signal amplitude can be used to determine the location of the defect (from the sensor position) and its severity.

Figure 4:
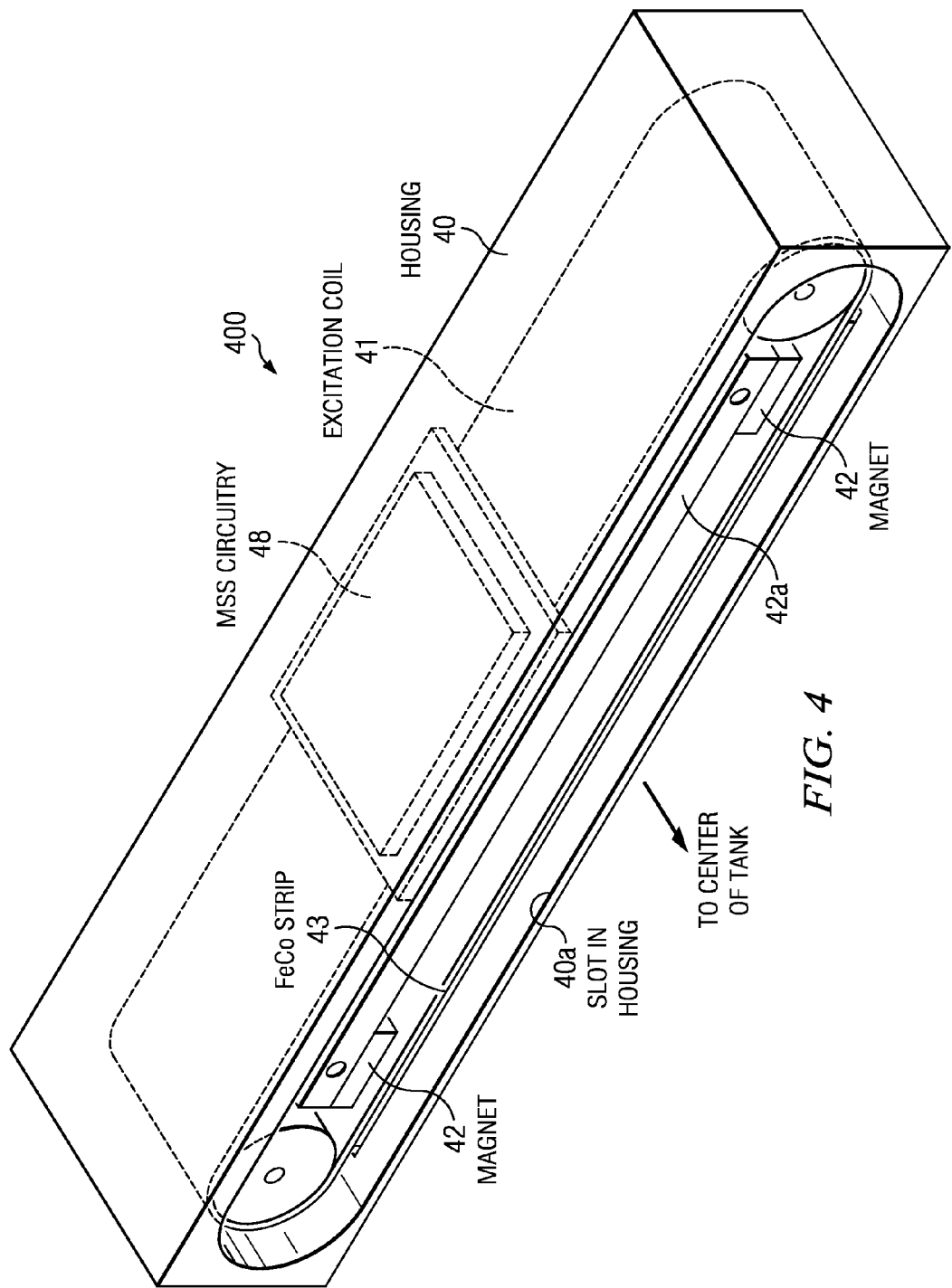
FIG. 4 illustrates the sensor with a housing for the operating components.

FIG. 4 is a perspective view of another embodiment of sensor 100, identified as sensor 400. Sensor 400 is shown with a housing 40. Housing 40 has a size and shape that generally conforms to the internal components of sensor 400, namely the coil 41, magnet 42, and circuitry 48. A slot 40a in housing 40 permits these internal components to be slid into housing 40 from its side. Housing 40 is preferably made from a non-ferromagnetic material, such as a plastic, and slot 40a is open to the bottom of housing 40, so that strip 43 may adhere to the bottom of coil 41. In the example of FIG. 4, housing 40 has a rectangular shape.

FIG. 4 further illustrates how sensor 400 is placed such that its "wide" dimension faces into the tank. The active region of the sensor 400, and the sensor beam width, are determined by the overlapping areas of the magnetostrictive strip 43, the bias field from magnet 42, and the electronic coil 41. Therefore, the beam width will generally be determined by the shortest of the three. Technically, in this design, that is probably the horseshoe-shaped magnet.

Referring again to FIGS. 1 and 2, an important feature of sensor 200 is its portability. It can be used to introduce ultrasonic guided waves in the tank bottom floor from the outside edge of the tank using a shear couplant. This eliminates the need for bonding of a magnetostrictive material to the outside edge of the tank bottom.

Figure 5:
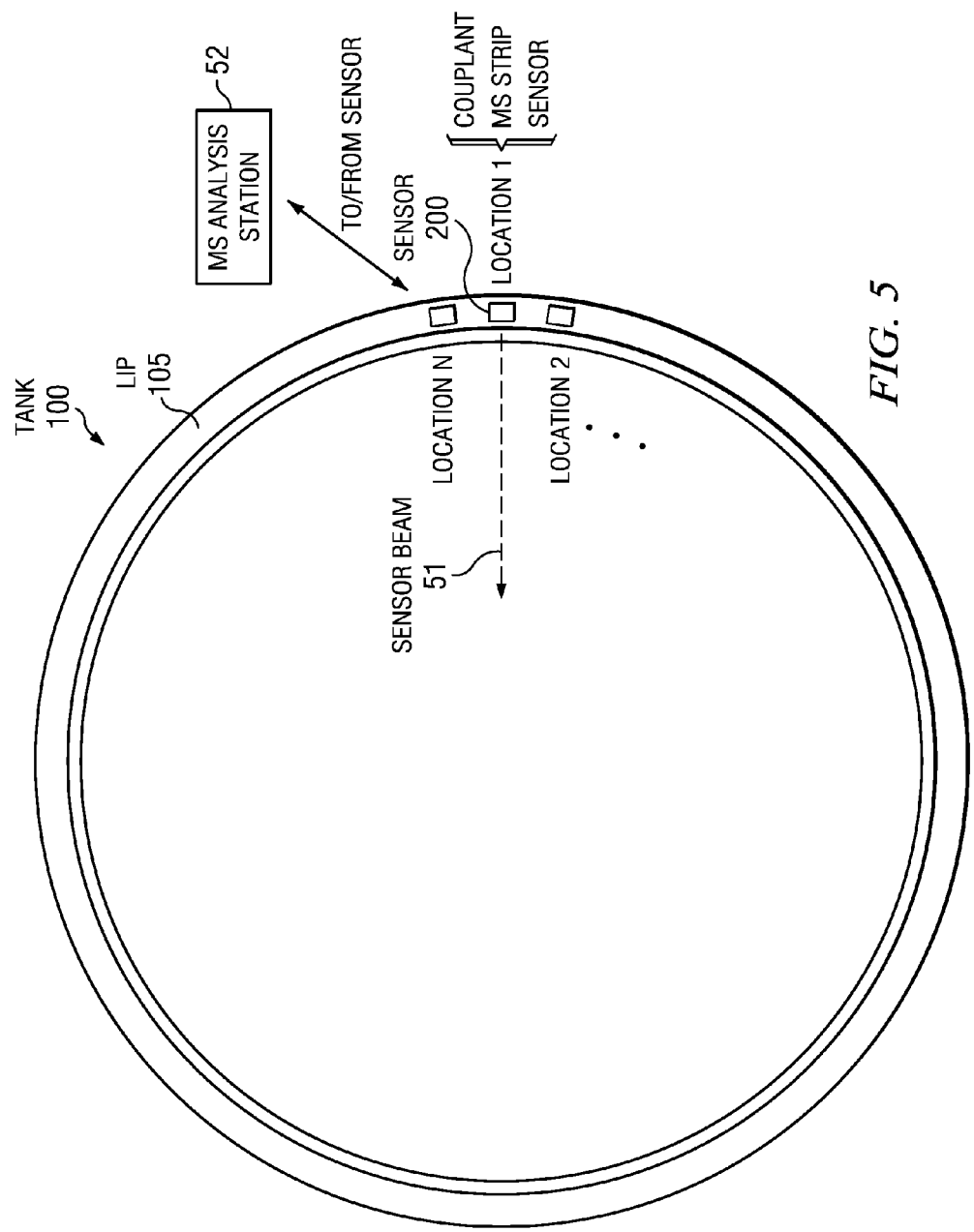
FIG. 5 illustrates a method of testing an above-ground tank using a magnetostrictive sensor.

FIG. 5 illustrates a method of testing a tank bottom for defects, using sensor 200, of which probes 300 and 400 are suitable embodiments. FIG. 5 is illustrative and the relative sizes of the sensor, the tank, and the various sensor locations are not intended to be in scale.

In operation, sensor 200 is moved circularly to different locations around the lip of the tank, eventually moving around the entire tank circumference. The expected range of sensor 200 is at least 3-4 meters towards the center of the tank bottom.

An example sensor 200 with a 3-4 meter range has a transmitted beam 51 approximately 250 mm wide. This beam spreads in a predictable manner, i.e., the half angle is calculated from the inverse sine of the wavelength divided by the length of the probe.

At each location, e.g., Location 1, Location 2 . . . Location N, a couplant is first applied to the lip 105. The couplant need only be applied to a spot slightly larger than the bottom surface of the sensor 200. Next, the sensor 200 is placed on the surface of the lip 105 over the couplant.

Once the sensor 200 is in place, it receives an appropriate excitation signal from the computer-implemented MsS analysis station 52. The sensor receives any defect signal returned from the material of the tank bottom, and delivers (via a wired or wireless connection) any such signals to the analysis station 52 for analysis and appropriate output.

When testing has been performed at one sensor location, the sensor 200 is picked up from its current location on lip 105 and moved to a next location on lip 105. The incremental radial distance that the sensor is moved is a function of the beam width and range of the probe, which in turn, are determined by the sensor design. As indicated above, it is expected that a practically built sensor will have a range of at least 3-4 meters toward the center of the tank bottom. It is further expected that the sensor will have a range toward the center of the tank to at least the weld of the first (outer) plate of the tank bottom.

As sensor 200 is moved around the circumference of the tank, it may be manually picked up and replaced in appropriate locations. If necessary or desired, a lever device may be used to pry the sensor from the tank lip.

What is claimed is:

1. A method of testing for defects in the bottom of an above ground storage tank, the tank bottom having a lip extending outwardly from the tank wall around the circumference of the tank, comprising:

Placing a couplant on the lip surface;

Placing a magnetostrictive sensor over the couplant, the sensor having at least a magnet for providing a magnetic bias, a coil for sending and receiving acoustic or ultrasonic signals into the tank bottom, a strip of magnetostrictive material bonded to the bottom of the coil, and circuitry for sending and receiving the signals to and from a magnetostrictive analysis station;

Wherein the sensor emits a beam that extends inwardly into the tank bottom toward the center of the tank bottom;

Operating the sensor in pulse echo mode to receive signals from defects in the bottom of the tank;

Lifting the sensor from the lip;

Moving the sensor to a next location on the lip; and

Repeating the preceding steps until the sensor has been placed in a series of locations around the circumference of the tank.

2. The method of claim 1, wherein the sensor has a range of at least 3 meters toward the center of the tank.

3. The method of claim 1, wherein the tank has a number of bottom plates, and the sensor has a range that extends inwardly for at least the radial distance of the first plate.

4. The method of claim 1, wherein the beam has a known beam width and the step of moving the strip and the magnetostrictive sensor is performed such that the beam width in each location is overlaps that of the prior location.

5. The method of claim 1, wherein the magnetostrictive material is FeCo.

6. The method of claim 1, wherein the magnet is horseshoe-shaped and the coil encircles the length of the magnet.

7. The method of claim 1, wherein magnet and coil are rectangular in dimension, and the step of placing a sensor is performed such that a long side of the magnet and coil are proximate the outer surface of the tank.

8. A magnetostrictive sensor system for testing for defects in the bottom of an above ground storage tank, comprising:

a magnetostrictive sensor, the sensor having at least a magnet for providing a magnetic bias, a coil for sending and receiving acoustic or ultrasonic signals into the tank bottom, a strip of magnetostrictive material bonded to the bottom of the coil, and circuitry for sending and receiving the signals to and from a magnetostrictive analysis station;

wherein the coil encircles the length of the magnet;

Wherein the sensor is configured to be electrically activated such that it emits a beam that extends inwardly into the tank bottom toward the center of the tank bottom;

Wherein the sensor is further configured to be operated in pulse echo mode to receive signals from defects in the bottom of the tank; and A housing generally conforming to the outer dimensions of the probe, having a slot for receiving the probe, the slot being open at the bottom of the housing so that the housing does not cover the strip.

9. The system of claim 8, wherein the sensor has a range of at least 3 meters.

10. The system of claim 8, wherein the magnetostrictive material is FeCo.

11. The system of claim 8, wherein the tank has a number of bottom plates, and the sensor has a range that extends inwardly for at least the radial distance of the first plate.

12. The system of claim 8, wherein the magnet is horseshoe-shaped and the coil encircles the length of the magnet.

\* \* \* \* \*